United States Patent [19]

Snell et al.

[11] 4,409,416

[45] Oct. 11, 1983

[54] LIGNIN CRACKING PROCESS USING FAST FLUIDIZED BED REACTIONS

[76] Inventors: George J. Snell, 112 Arlington Dr., Fords, N.J. 08863; Derk T. A. Huibers, 37 Abey Dr., Pennington, N.J. 08534

[21] Appl. No.: 353,314

[22] Filed: Mar. 1, 1982

[51] Int. Cl.³ .......................... C07C 1/00; C07C 1/20
[52] U.S. Cl. ...................................... 585/635; 201/34; 585/469; 585/636; 585/639
[58] Field of Search ................ 208/125, 126, 127; 568/806; 585/635, 638, 639, 469; 201/34, 38

[56] References Cited

U.S. PATENT DOCUMENTS 3,105,095 4/1959 Oshima et al. ............... 568/383

*Primary Examiner*—Delbert E. Gantz
*Assistant Examiner*—A. Pal

[57] ABSTRACT

A process for cracking lignin-containing feed materials, such as precipitated from black liquor, to produce hydrocarbon products such as ethylene, utilizing dual fluidized beds of particulate solids in series flow arrangement. In the process, the feedstock is introduced with a diluent gas such as steam into the first or fast fluidized bed for cracking reactions at superficial gas velocity exceeding about 5 ft/sec. A particulate solids carrier material, which can comprise at least partly coke produced in the process, is circulated between the beds, and coke deposited on the carrier in the first or cracking bed at 1000°–1600° F. temperature is burned off in a second or combustion bed maintained at 1400°–2000° F. temperature by an oxygen-containing gas and diluent steam introduced therein. Superficial upward gas velocity in the fast fluidized bed zone exceeds about 5 ft/sec. and the bed density exceeds about 3 lb/cu.ft. If desired, some externally supplied particulate solids carrier material also can be used in the process. Also, supplemental fuel can be supplied to the slow bed combustion zone if needed to maintain the desired temperature therein.

12 Claims, 1 Drawing Figure

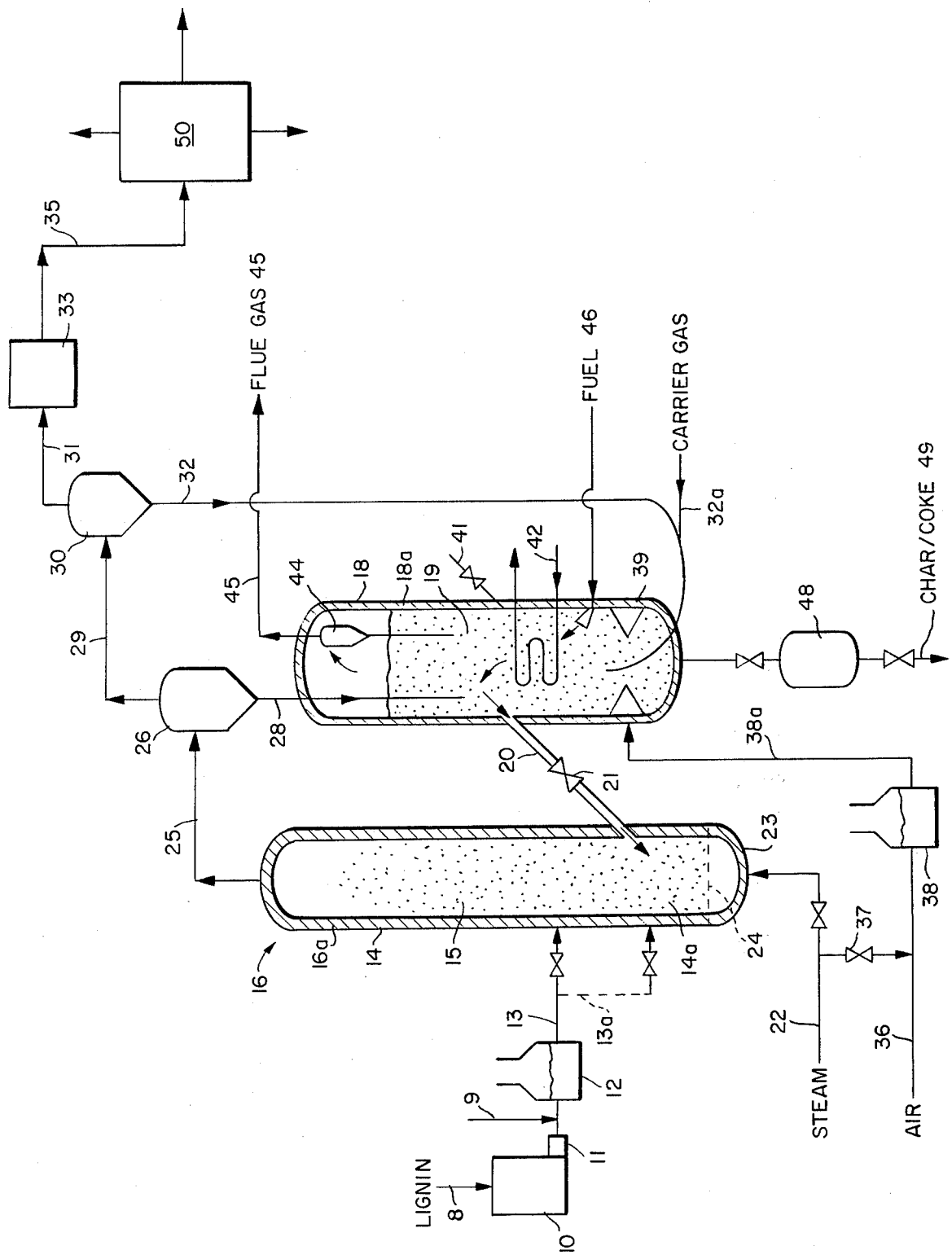

(1)

LIGNIN CRACKING PROCESS USING FAST FLUIDIZED BED REACTIONS

BACKGROUND OF INVENTION

This invention pertains to a process for cracking lignin-containing feed materials in a fast fluidized bed reaction zone operating at high gas velocities and low residence times to produce useful aromatic and paraffinic hydrocarbon products and olefins such as ethylene.

Lignin is a by-product of wood pulping operations, and is currently utilized as a fuel in modern paper mill practice. Chemically, lignin can be considered as a three dimensional condensation product of coniferyl, p-coumaryl and sinapyl alcohols. While coniferyl alcohol is dominant, the ratios of the three alcohols depend on the type of wood used. Hardwoods have more sinapyl alcohol. Some technologists symbolize the coniferyl building unit of lignin as R-C-C-C, in which R represents the 4-hydroxy-3-methoxy phenyl group, which is also referred to as the guaiacyl group. Lignin is a major constituent in a principal by-product stream from paper mills, usually called "black liquor". If desired, lignin-like material can be precipitated from black liquor by salting out, by changes of pH value, and by the addition of certain cations.

Various methods for conversion of lignin and lignocellulose materials to produce fuel gas and chemicals have been previously disclosed, including U.S. Pat. No. 4,164,397 to Hunt et al, which uses a downflow stirred reactor, U.S. Pat. No. 4,166,830 to Guth et al which discloses a cracking process in multiple reactors at high velocities using atomizing nozzles. A process for cracking petroleum feedstocks to produce ethylene in an elongated reactor at short residence times not exceeding about 2 seconds is disclosed in U.S. Pat. No. 4,061,562 to McKinney. Also, the gasification of coal using a fluidized bed of char particles at high superficial gas velocity is disclosed by U.S. Pat. Nos. 3,840,353, 3,957,457, and 3,957,458 to Squires. However, reactions utilizing fast fluidized bed contacting techniques have apparently not previously been used for thermally cracking lignin-containing feedstocks to control reaction time and produce desirable aromatic chemical products. The fast fluidized bed contacting regime has been found especially useful in controlling cracking severity and limiting residence times.

SUMMARY OF INVENTION

The present invention provides a process for cracking lignin-containing feed materials to produce useful aromatic and paraffinic hydrocarbon liquid and olefinic gas products, and uses fast fluidized bed contacting at conditions of high temperature, short residence time and low pressure. In the process, the lignin-containing feed material is fed with a diluent gas into a cracking zone containing a fast fluidized bed of particulate solids carrier material operating at high upward superficial gas velocities exceeding about 5.0 ft/sec. The normally endothermic cracking reactions for the feed occur in the fast fluidized bed and produce a crackate vapor material along with coke, which can be deposited on and within the particulate solids carrier material. Also, the particulate solids carrier material can comprise at least partly coke produced in the cracking reactions.

The crackate material along with indigenous coke-like or coke-laden particulate solids carrier material is passed continuously from the fast fluidized bed to a solids separation step, from which the particulate solids carrier material is passed to a combustion zone containing a normal or "slow" fluidized bed, wherein coke is combusted and the resulting hot particulate solids carrier material is recycled to the fast fluidized bed to provide the sensible and endothermic heat requirements for the feed material cracking reaction in the fast fluid bed. A fast fluidized gas-solid contacting regime is maintained in the cracking zone into which the feed material, diluent gas, and recycled particulate solids heat carrier material are continuously fed, usually as separate streams. From the solids separation step, a hydrocarbon vapor effluent product stream is withdrawn for further processing.

BRIEF DESCRIPTION OF DRAWING

FIG. 1 is a schematic flow diagram of a lignin cracking process using a fast fluidized bed reaction zone.

DESCRIPTION OF INVENTION

In accordance with this invention, useful process conditions which characterize operations in the fast fluidized bed cracking zone are a temperature range of 1200°–1700° F., average residence times of 0.05 to 5.0 seconds and operating pressures of 1.0 to 10.0 atmospheres. The diluent gas used can be steam, nitrogen or carbon dioxide, with steam usually being preferred because of its availability, low cost, and good heat transfer characteristics. When steam diluent is used, useful steam/feed material weight ratios are in the range of 0.5–5.0. The fast fluidized bed density usually exceeds about 3.0 lb/cu.ft, and preferably is 5 to 25 lb/cu.ft. Because of the fast fluidized condition of the particulate solids carrier material and the high degree of back-mixing which occurs in the bed, the reaction zone operates at substantially isothermal conditions, i.e. having temperature difference not exceeding about 20° F. across the bed, which is in contrast to conventional tubular furnace type reactors or entrained bed reactors which have a substantial temperature change from inlet to outlet across the reactor. The diluent steam is advantageously fed to the fast fluidized bed cracking zone as a fluidizing gas and also to moderate the cracking reaction by controlling partial pressure in the vapor phase. The diluent steam can be superheated as needed to provide heat to the cracking zone.

A crackate effluent material is withdrawn from the fast fluidized bed cracking zone, along with particulate solids carrier material, and after separation of the particulate solids carrier from the effluent crackate vapor stream, the carrier material then is passed into the slow fluidized bed combustion zone, where the temperature is maintained higher than the cracking temperature used in the fast bed. The particulate solids carrier material entering the slow bed combustion zone is heated, and a portion of the coke is burned in the slow bed at temperature within the range of 1400°–2000° F. Sufficient oxygen-containing gas is introduced into the slow bed combustion zone to maintain the temperature therein within the desired range. When feeding lignin-containing feedstocks having low carbon residue contents for cracking in the fast bed, some indigenous fuel firing may be required in the combustion zone to supplement the heat produced from combusting the coke. The heat carrier material circulation rates used are sufficient to maintain the process heat balance in the cracking zone.

The particulate heat carrier material can comprise indigenous coke produced in the process. However, if such coke does not have the desired particle size in a range of 20–200 microns, some supplemental particulate solids carrier material can be provided from an external source. Such external particulate solids carrier material used in the process should be inert and must have a softening or melting temperature at least about 100° F. above the maximum temperature used in the combustion zone slow fluidized bed, and particulate solids with melting points in excess of 2000° F. are normally employed. Other desirable physical characteristics for the particulate carrier material are good thermal stability, adequate porosity, resistance to sintering and good abrasion resistance. When coke particles which are formed in the process are used as carrier material, additional coke can be deposited thereon in the fast fluidized bed cracking zone and is burned off in the slow fluidized bed combustion zone. Fresh external particulate solids carrier material can be added to the circulating carrier solids, if desired, via a solids feeder device, such as a lockhopper. Also, particulate solids carrier material can also be purged from the system, if and as required.

The effluent crackate stream from the fast fluidized bed cracking zone contains gas and coke solids, and can advantageously be quenched with a cooler gas or oil stream to limit the extent of the cracking reactions. The quenched stream containing gaseous product and particulate solids carrier material is then separated, in a solids-separation step and the particulate solids carrier material is passed to the slow fluidized bed. The resulting product gas stream containing olefins can be purified in subsequent process steps, such as partial condensation, extraction or fractionation to remove undesired compounds and enrich the product.

In the present invention, lignin-like materials can be fed to the fast fluidized bed cracking zone either as an aqueous solution, slurry or paste, or a solid. The $C_3$ bridges between predominantly mono-ring guaiacyl moieties are amenable to steam thermal cracking. In addition, dehydration, dehydrogenation, and dealkylation processes will occur simultaneously with the principal cracking reactions at elevated temperatures. Gaseous hydrocarbon (mostly ethylene) formed during the destructive cracking of bridging units will react further in the vapor phase with the concomitant production of other light hydrocarbons such as methane, propylene, butadiene, and some acetylene. Thus, the primary products of this lignin cracking process are methyl catechol, ethylene, and carbon monoxide. Methyl catechol is converted quickly to catechol, cresol, phenol, toluene, and benzene when process severity is increased. In addition, part of the ethylene is converted to methane, propylene, butadiene, benzene and acetylene. By-product vapor phase hydrolysis reaction, which results in low molecular weight oxygenated organic compounds (alcohols, aldehydes, ketones, and acids) are also produced at certain process severities when water is present in the cracking zone. Mono-ring aromatics, phenols, and cresols are major products when process severity is increased.

Several advantages are provided by this fast fluidized bed lignin cracking process. It uses a low cost feedstock, and undesirable heavy liquid and semi-coke-like by-products are used to satisfy the energy requirements of the process. Very short residence times are employed and the vapor phase residence time and temperature conditions in the reaction zone are easily controlled. It is a low pressure process which requires no costly hydrogen addition. Also, this fast fluidized bed cracking process is characterized by low capital and operating cost compared to conventional hydrocracking processes, and it should provide a high percentage of on-stream time.

DESCRIPTION OF PREFERRED EMBODIMENT

As shown by FIG. 1, a lignin or lignin-containing feedstock material is provided at 8 and is treated at 10, such as by a precipitation step to increase the lignin concentration above about 50% and preferably to 70–95 W %. The concentrated material is pressurized by feeder device 11, a carrier gas such as steam or a recycled process gas is added at 9, and the material is preheated at 12 to 400°–600° F. temperature. The heated material is fed continuously thru conduit 13 and/or 13a into cracking zone 14, containing a fluidized bed 15 in which a particulate solids carrier material such as carbonaceous or char-like particles are maintained in a fast fluidized bed condition for heating the feed and producing rapid cracking reactions. The bed 15 uses high superficial gas velocities in the range of 5–20 ft/sec and low residence times. The feedstock and steam usually enter the lower portion 14a of the cracking zone 14 of reactor 16, having refractory lining 16a. Cracking conditions in bed 15 are maintained within the ranges of 1200°–1700° F. temperature, 0.3–3 sec. residence time, and 1–10 atmospheres pressure. A char-like particulate solid heat carrier material is continuously recycled to the cracking zone 15 from adjacent slow fluidized bed combustion zone 18 thru transfer conduit 20 and control valve 21 at a temperature in excess of the cracking zone temperature to supply heat to the cracking zone fluidized bed 15. The solids density maintained in the fast fluid bed is at least about 3 lb/cu.ft and is usually in a range of 5–25 lb/cu.ft. Superheated steam is supplied to the cracking reactor via line 22 to provide fluidizing gas and control the hydrogen partial pressure therein and flows thru a plenum chamber 23 located in the bottom of the cracking reactor 16. The steam is uniformly dispersed into the lowest portion 14a of the cracking zone 14 via a flow distributor 24, such as a perforated plate, porous element or an equivalent device.

Cracked effluent vapors along with entrained carbonaceous or char-like solids (coke) exit from the cracking zone 14 upper end thru conduit 25 and enter a primary gas solids separator or cyclone 26, in which the particulate solids are separated from the vapor. The solids flow continuously downward thru a dipleg conduit 28 into the slow fluid bed combustion zone 18. Gas stream 29 from the primary separator 26 is fed to a normally close-coupled secondary gas-solids cyclone separator 30. Fine char or char containing solid particles separated in the secondary cyclone 30 are returned thru a conduit 32 to the lower portion of the slow fluid bed 19 in combustion zone 18. Effluent cracked vapor product at 31 from the secondary cyclone separator 30 is quenched at 33 in an in-line or transfer line device using compatible quench liquid 34. Quenched cracked product stream at 35 is fed to recovery-separation-purification steps 50.

The slow fluidized bed 19 in combustion zone 18 has a larger diameter than fast fluidized bed 15 and operates with upward superficial gas velocity in a range of 0.3 to 3.0 ft/sec. Air at 36 and steam 37 are heated at 38 and the heated air-steam mixture is fed thru conduit 38a into a flow distributor grid 39 located in the lower portion of the fluid bed combustion zone 18, having a refractory lining 18a. If desired, some supplemental particulate solids carrier material can be added to the process as seed material to promote formation of coke particles having the desired particle size and coke carrying characteristics. Such added particles can comprise petroleum-derived coke, silica, alumina, and other such materials. The particulate solids added are preferably introduced into the slow bed at 41 through a lock-hopper device. Also, heat exchanger surfaces 42 can be located in the lower portion of the combustion zone for steam generation, if desired. Flue gas from the fluid bed combustion zone is passed thru an internal cyclone separator 44 and withdrawn at 45. Supplementary solid or heavy liquid fuel at 46 can be optionally fired in the fluid bed combustor if required or desired. Although there will usually be no excess char formed in the system, a purge char/coke by product stream 49 intended for utilization in a steam generating plant can be withdrawn from the bottom of the fluid bed combustor thru a hot char/coke lock hopper type receiver 48.

This invention will be further illustrated by the following examples, which should not be construed as limiting in scope.

EXAMPLE

A lignin-containing material precipated from black liquor is preheated to about 500° F. and introduced with steam into the lower end of a fast fluidized bed reaction zone having a configuration similar to FIG. 1, and in which the bed of carrier material is maintained at about 1500° F. temperature. The feed material is cracked while passing upwardly through the bed at superficial velocity exceeding 5.0 ft/sec to produce a crackate material. Vapor residence time in the cracking zone is about 1.0 second.

The effluent crackate vapor is separated from particulate solids in a cyclone separator, and the solids containing coke deposits are passed into the upper end of an ordinary or slow fluidized bed combustion zone maintained at about 1600° F. temperature for combustion of coke. Heated air and superheated steam are introduced into the lower end of the slow fluidized bed combustion zone. The hot decoked solids are recycled to the lower end of the fast fluidized bed, and flue gas is withdrawn from the top of the slow bed. The typical product slate that is obtained if secondary reactions are minimized is given in Table 1, with methyl catechol being the principal product. Increased process severity produces more secondary conversion of methyl catechol to catechol, cresol, phenol, toluene, and benzene. In addition, some tar is formed.

TABLE 1
TYPICAL YIELDS FROM LIGNIN CRACKING WITH STEAM

| | W % of Organic Lignin |
|---|---|
| CO | 10.4 |
| $CO_2$ | 10.9 |
| $CH_4$ methane | 3.6 |
| $C_2H_4$ ethylene | 10.4 |
| $C_3$, $C_4$, olefins (propane, butane) | 1.7 |
| TOTAL GASES | 37.0 |
| Benzene | 1.7 |
| Phenol | 11.3 |
| p-cresol | 19.8 |
| m-cresol | 9.0 |
| catechol | 5.0 |
| methyl catechol | 4.5 |
| tar | 11.7 |

TABLE 1-continued
TYPICAL YIELDS FROM LIGNIN CRACKING WITH STEAM

| | W % of Organic Lignin |
|---|---|
| TOTAL LIQUIDS | 63.0 |

Although this invention has been disclosed broadly and in terms of the accompanying drawing and preferred embodiments, it will be appreciated by those skilled in the art that adaptations and modifications of the process can be made within the spirit and scope of the invention, which is defined solely by the following claims.

We claim:

1. A process for cracking lignin-containing materials to produce hydrocarbon products, comprising:
   (a) feeding lignin-containing feed material with a diluent gas into a cracking zone containing a fast fluidized bed of particulate solids carrier material, and maintaining the bed within a temperature range of about 1200°–1700° F. and at an average residence time less than about 5.0 seconds to crack the feed material and produce a crackate material and coke, while depositing coke on the particulate solids carrier material;
   (b) passing the crackate effluent from said cracking zone along with said particulate solids carrier material containing coke to a solids separation step, and then passing the solids to a combustion zone containing a slow fluidized bed of said particulate solids carrier material containing coke maintained at higher temperature then in said cracking zone;
   (c) introducing oxygen-containing gas and steam into the slow fluidized bed to maintain it within a temperature range of about 1400°–2000° F. for combustion of coke;
   (d) recycling said particulate solids carrier material from said combustion zone to the lower end of said fast fluidized bed cracking zone at a controlled rate to provide process heat therein; and
   (e) withdrawing a hydrocarbon vapor effluent product from the solids separation step.

2. The process of claim 1, wherein the fast fluidized bed in said cracking zone is maintained at 1200°–1600° F. temperature, at residence times of 0.05–4.0 seconds, and upward superficial gas velocities exceeding about 5.0 ft/sec.

3. The process of claim 1, wherein the diluent gas is steam.

4. The process of claim 1, wherein the steam to feed material weight ratio in the cracking zone is within a range of 0.5–5.0.

5. The process of claim 1, wherein the particulate solids carrier material is selected from the group consisting of coke, alumina, and silica-alumina, and combination thereof.

6. The process of claim 1, wherein the particulate carrier material has particle sizes in a range of 100–350 mesh (U.S. Sieve Series).

7. The process of claim 1, wherein external particulate solids carrier material is added to the process.

8. The process of claim 1, wherein particulate solids carrier material is removed from the process.

9. The process of claim 1, wherein supplemental fuel is added to the combustion zone in an amount sufficient to maintain said zone in a temperature range of 1400°–2000° F.

10. The process of claim 1, wherein the cracking zone effluent stream along with particulate solids carrier material containing coke are passed to a primary solids separation step, from which the separated effluent is passed to a secondary solids separation step, and said particulate solids carrier material removed from each solids separation step is passed to said slow fluidized bed in said combustion zone.

11. The process of claim 1, wherein particulate solids carrier material in said slow fluidized bed are fluidized by upward superficial gas velocities of 0.3–3.0 ft/sec, and combustion flue gases are withdrawn from said combustion zone.

12. A process for cracking lignin-containing materials to produce hydrocarbon products, comprising:

(a) feeding lignin-containing feed material with diluent steam into a cracking zone containing a fast fluidized bed of particulate solids carrier material, maintaining the bed within a temperature range of about 1200°–1700° F., at an average residence time of about 0.05–3 seconds, and at a pressure range of 1–10 atmospheres to crack the feed material and produce a crackate material and coke, while depositing coke on the particulate solids carrier material;

(b) passing the crackate effluent from said cracking zone along with said particulate solids carrier material containing coke to a primary solids separation step, and then passing the particulate solids carrier material therefrom to a combustion zone containing a slow fluidized bed of the carrier material maintained at higher temperature than in said cracking zone;

(c) passing the crackate effluent along with some particulate solids carrier material from said primary separation step to a secondary solids separation step, from which the remaining particulate solids carrier material is returned to the lower end of said combustion zone;

(d) introducing oxygen-containing gas and steam into the slow fluidized bed to maintain it within a temperature range of about 1400°–2000° F. for combustion of coke;

(e) recycling said particulate solids carrier material from said combustion zone to the lower end of said fast fluidized bed cracking zone at a controlled rate to provide process heat therein; and (f) withdrawing a hydrocarbon vapor effluent product from the secondary solids separation step.

* * * * *